United States Patent [19]

Plitt et al.

[11] Patent Number: 5,585,266
[45] Date of Patent: Dec. 17, 1996

[54] IMMOBILIZED CELL BIOREACTOR

[76] Inventors: Cheryl A. Plitt, R.R. 2, Plainfield, Wis. 54966; Wendall J. Harris, deceased, late of Ripon; by Dorothy B. Harris, legal representative, 518 Newbury, Ripon, both of Wis. 54971

[21] Appl. No.: 538,976

[22] Filed: Oct. 5, 1995

[51] Int. Cl.$^6$ ............................. C12N 5/00; B01D 33/70
[52] U.S. Cl. ................. 435/240.23; 435/240.241; 435/240.45; 435/299.1; 210/150; 210/615
[58] Field of Search ................ 435/299.1, 240.23, 435/240.241, 240.45; 210/150, 615

[56] References Cited

U.S. PATENT DOCUMENTS

| | | | |
|---|---|---|---|
| 4,122,011 | 10/1978 | Strigle, Jr. | 210/150 |
| 4,137,171 | 1/1979 | Yokata | 210/150 |
| 4,665,027 | 5/1987 | Dale et al. | 435/162 |
| 4,689,301 | 8/1987 | Adet et al. | 435/284 |
| 4,789,634 | 12/1988 | Muller-Lierheim et al. | 435/288 |
| 4,925,803 | 5/1990 | Suehiro et al. | 435/288 |
| 5,079,161 | 1/1992 | Mitsuda et al. | 435/240.23 |
| 5,079,168 | 1/1992 | Amiot | 435/284 |
| 5,264,129 | 11/1993 | Simpson et al. | 210/611 |
| 5,376,548 | 12/1994 | Matsuo et al. | 435/299.1 |

FOREIGN PATENT DOCUMENTS

PCT/US89/
02228 11/1989 WIPO.

*Primary Examiner*—David A. Redding
*Attorney, Agent, or Firm*—DeWitt Ross & Stevens SC

[57] ABSTRACT

An immobilized cell bioreactor is disclosed wherein the cells are harbored within or upon an immobilization matrix including cell support sheets comprised of common textile fabric. The cell support sheets are oriented in a vertical parallel layered array with a gas phase substantially surrounding each sheet. The vertical orientation allows nutrient culture supply and product recovery to be assisted by gravity. The vertical orientation also allows the sheets to extend into unused vertical space, producing a space-efficient bioreactor, and it also allows a series of bioreactors to be closely and efficiently organized within the laboratory space.

20 Claims, 2 Drawing Sheets

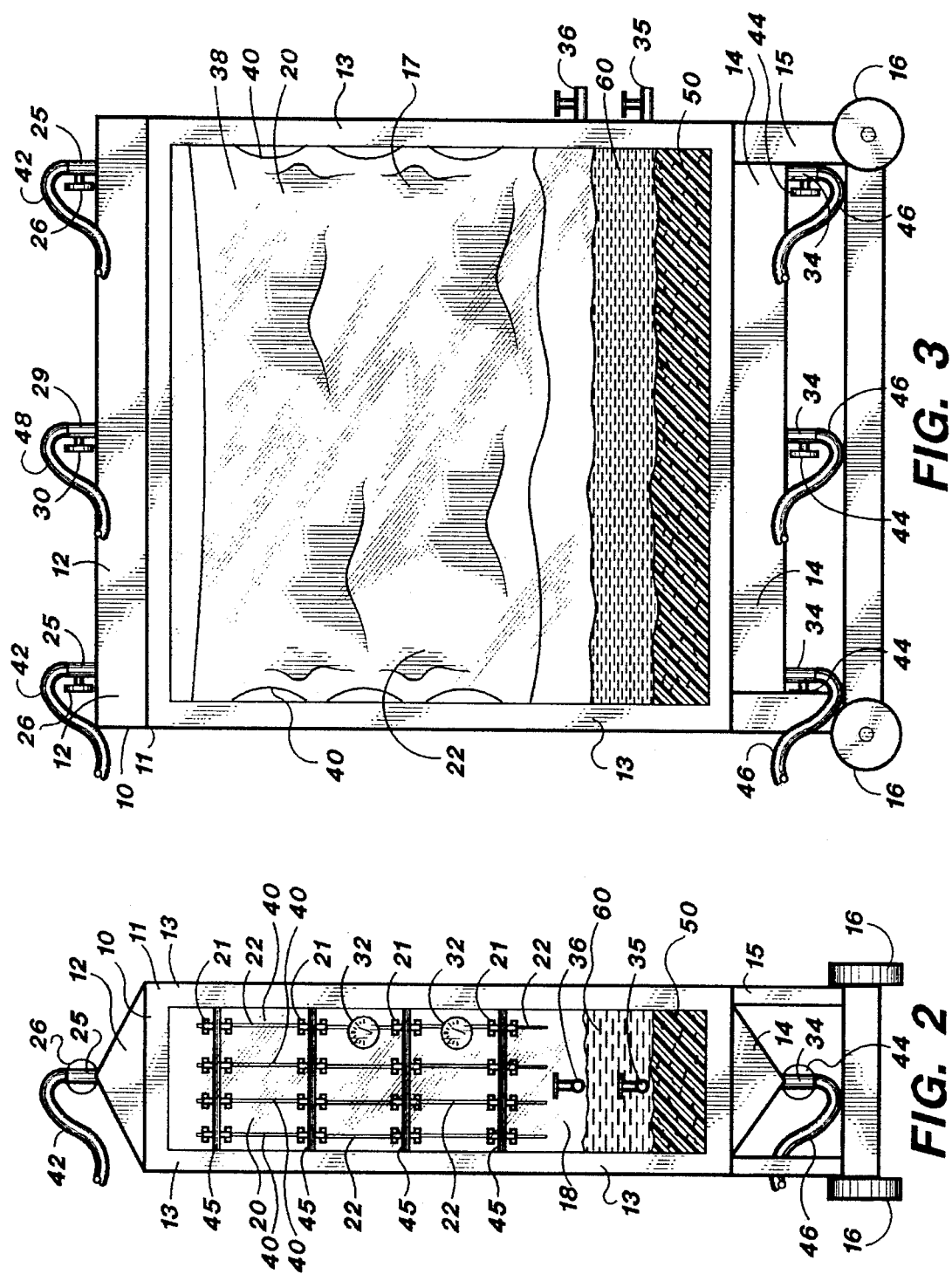

IMMOBILIZED CELL BIOREACTOR

FIELD OF THE INVENTION

The present invention relates generally to a bioreactor for culturing and harvesting products produced by immobilized cells, and specifically to an apparatus for a low-cost space-efficient immobilized cell bioreactor.

BACKGROUND OF THE INVENTION

Many industries and research facilities grow living cells for use in their manufacturing and research processes. Such cells may include microorganisms (such as bacteria, fungi, etc.) or cells from human, animal, plant, or other tissues. The cells are generally grown in vitro, and their environment is engineered to coerce the cells into producing some desired cell product, generally acids, enzymes, proteins, vitamins, bacteria, fungi, or other metabolic by-products, e.g., ethanol and penicillin, or more cells per se, e.g., yeast.

The prior art reveals various apparatuses for culturing cells and harvesting cell products produced by these cells. These apparatuses, frequently referred to in the art as bioreactors, include immobilized cell bioreactors wherein the cells to be cultured are immobilized by affixing them to components of the bioreactor. The cells are usually permanently or temporarily entrapped upon, within, or behind an immobilization matrix or membrane containing cell support surfaces, usually porous surfaces or surfaces having a gel or an electric field thereupon. A nutrient cell culture solution is supplied to the cell support surfaces so that the cells may feed upon it. As the cells feed upon the nutrient cell culture solution, they produce the desired cell product, generally either more cells or some cell byproduct. The nutrient cell culture solution (or some other carrier medium) carries the cell product and other cell wastes away from the cell support surfaces. The cell product may then be removed from the bioreactor in batches, or it may be removed continuously by collecting the cell product from the outgoing nutrient stream or from a separate cell product stream.

The prior art discloses a number of different types of bioreactors which utilize either continuous or batch processes to produce and harvest cells and cell products and which surround the immobilization matrices with either gas phase or liquid phase media. Several examples follow.

U.S. Pat. No. 4,665,027 to Dale et al. discloses a continuous immobilized cell bioreactor with two stages, an enricher stage and a stripper stage. In the enricher stage, gas and a liquid containing nutrient cell culture solution are continuously introduced into the bottom of the enricher, where they flow co-currently upward past cells immobilized on ceramic saddles. The cells produce volatile by-products which are absorbed into the gas, which exits to a condenser. The liquid is then continuously introduced into the top of a stripper stage where it flows downward past cells immobilized on ceramic saddles. At the same time, gas is introduced into the bottom of the stripper to flow upward countercurrently to the liquid. As it does so, the gas absorbs the volatile by-product produced by the immobilized cells. While the liquid flows from the bottom of the stripper, the gas is released from the top of the stripper to flow to the condenser. The condenser collects a continuous flow of by-product.

U.S. Pat. No. 5,079,168 to Amiot discloses a continuous gas phase bioreactor having an immobilization matrix comprising a gas-permeable but liquid-impermeable rolled cell support sheet. The cell support sheet is rolled with liquid-permeable capillaries separating each layer of cell support sheet within the roll. These capillaries transport nutrient cell culture solution and remove waste products.

PCT publication WO89/11529 to Wu et al. discloses a continuous liquid-phase bioreactor including an immobilization matrix comprised of parallel cell support sheets upon which a gel serves as the cell support medium. A liquid phase flows past and between the cell support sheets, collecting and transporting the cell product to be harvested.

The prior art also reveals a great variety of alternative immobilization matrix configurations and cell support media. For example, U.S. Pat. No. 4,789,634 to Muller-Lierheim et al. discloses an immobilization matrix comprising a pressure resistant polymer bead matrix wherein the interstitial spaces between beads entrap and harbor the microorganisms. Capillaries within the beads allow for distribution of nutrient cell culture solution to the microorganisms, but do not allow the microorganisms to grow within the beads. The same reference also discloses an immobilization matrix made of sheets of beads organized in a parallel layered fashion.

Another example of an immobilization matrix is disclosed in U.S. Pat. No. 4,689,301 to Adet et al. This reference discloses a cell support medium comprising a transparent polyurethane foam cell support sheet. Microorganisms are harbored within pores in the sheet wall, and nutrient cell culture solution is supplied to the cell support sheet to feed the immobilized cells. Adet et al. also reveal a parallel layered arrangement of sheets.

U.S. Pat. No. 4,925,803 to Suehiro et al. discloses an immobilization matrix comprising a braided configuration of long, tubular filaments which is then rolled onto a tubular frame. The microorganisms become entrapped within the immobilization matrix, and nutrient cell culture solution is supplied in the axial direction through the frame.

Thus, the prior art shows a number of immobilized cell bioreactors involving parallel arrays of cell support media, some of which are gas phase and some of which are liquid phase. However, all bioreactors in the prior art tend to be quite complex and expensive. First, the immobilization matrix tends to be made of specialized cell support media utilizing surface gels or precision-engineered surfaces including pores, capillaries, or interstitial spaces. Second, all bioreactors in the prior art tend to require expensive transport mechanisms which use pumps or other specialized equipment to transport the cell product and/or nutrient cell culture solution away from the immobilization matrix.

SUMMARY OF THE INVENTION

The present invention is directed to an immobilized cell bioreactor apparatus for culturing cells which produce cell product or by-product. The bioreactor apparatus comprises a tank including a base, a roof, two opposing face walls, and two opposing side walls. The tank further includes support means for supporting at least one cell support sheet within the tank. Such cell support sheets have two faces bounded by a sheet edge, and when such sheets are used in combination with the bioreactor apparatus, the support means support them from the sheet edge and maintain their faces in a substantially vertical orientation. Besides the tank, the bioreactor apparatus also includes feed means for dispensing nutrient feed stock into the tank, and recovery means for recovering a product produced by the cultured cells.

The present invention is also directed to a method for culturing immobilized cells which produce cell product or by-product in an immobilized cell bioreactor. The immobilized cell bioreactor used to practice the method includes a tank having a base, a roof, two opposing face walls, and two opposing side walls. The immobilized cell bioreactor further includes at least one cell support sheet having two faces bounded by a sheet edge, and support means which support the cell support sheet within the tank from the sheet edge so that the faces are maintained in a substantially vertical orientation. The method comprises the steps of introducing the cells onto the cell support sheet; supplying nutrient feed stock to the cells; and recovering cell product or by-product produced by the cells.

The immobilized cell bioreactor of the present invention has several advantages over the bioreactors of the prior art.

First, the immobilization matrix may use metal or plastic mesh or commonly available textile fabric materials, such as sheets, towels, or blankets made of terry cloth, felt, flannel, burlap, tweed, velvet, khaki, wool, canvas, linen, polyester, VELCRO, etc. for its cell support surfaces. Use of textile fabric materials within the immobilization matrix greatly reduces both the start-up and maintenance cost of the bioreactor.

Second, the cell support surfaces are arranged within the immobilization matrix in the common parallel layered arrangement, but the planes of the cell support surfaces are oriented vertically. This allows gravity-aided nutrient supply to the cell support surfaces and gravity-aided cell product recovery from the surfaces, reducing the cost of the bioreactor by eliminating the need for pumps and other machinery. The vertical orientation of the cell support surfaces also allows their own weight to support them in a parallel layered matrix without the use of spacers to separate them. This feature increases the efficiency of the bioreactor since such spacers can interfere with nutrient delivery to and cell product recovery from the cell support surfaces and increase pressure within the bioreactor, as well as lessen the space on the surfaces available for cells to grow. Further, this feature also allows for efficient temperature control of the bioreactor by use of a liquid or gas flow between the layered matrix.

Third, the vertical orientation of the cell support surfaces allows a very space-efficient bioreactor. The bioreactor of the present invention may be made with dimensions that extend quite high in the vertical direction, thereby utilizing space which is commonly unused because of its height. In addition, several bioreactors of this type may be closely placed next to each other for an extremely space-efficient organization of several bioreactors.

Further objects, features, and advantages of the invention will be apparent from the following detailed description when taken in conjunction with the drawings.

BRIEF DESCRIPTION OF THE DRAWINGS

FIG. 2 is a side elevational view of the bioreactor of FIG. 1.

FIG. 3 is a front elevational View of the bioreactor of FIG. 1.

DETAILED DESCRIPTION OF THE INVENTION

The Bioreactor Apparatus

Figure 1:
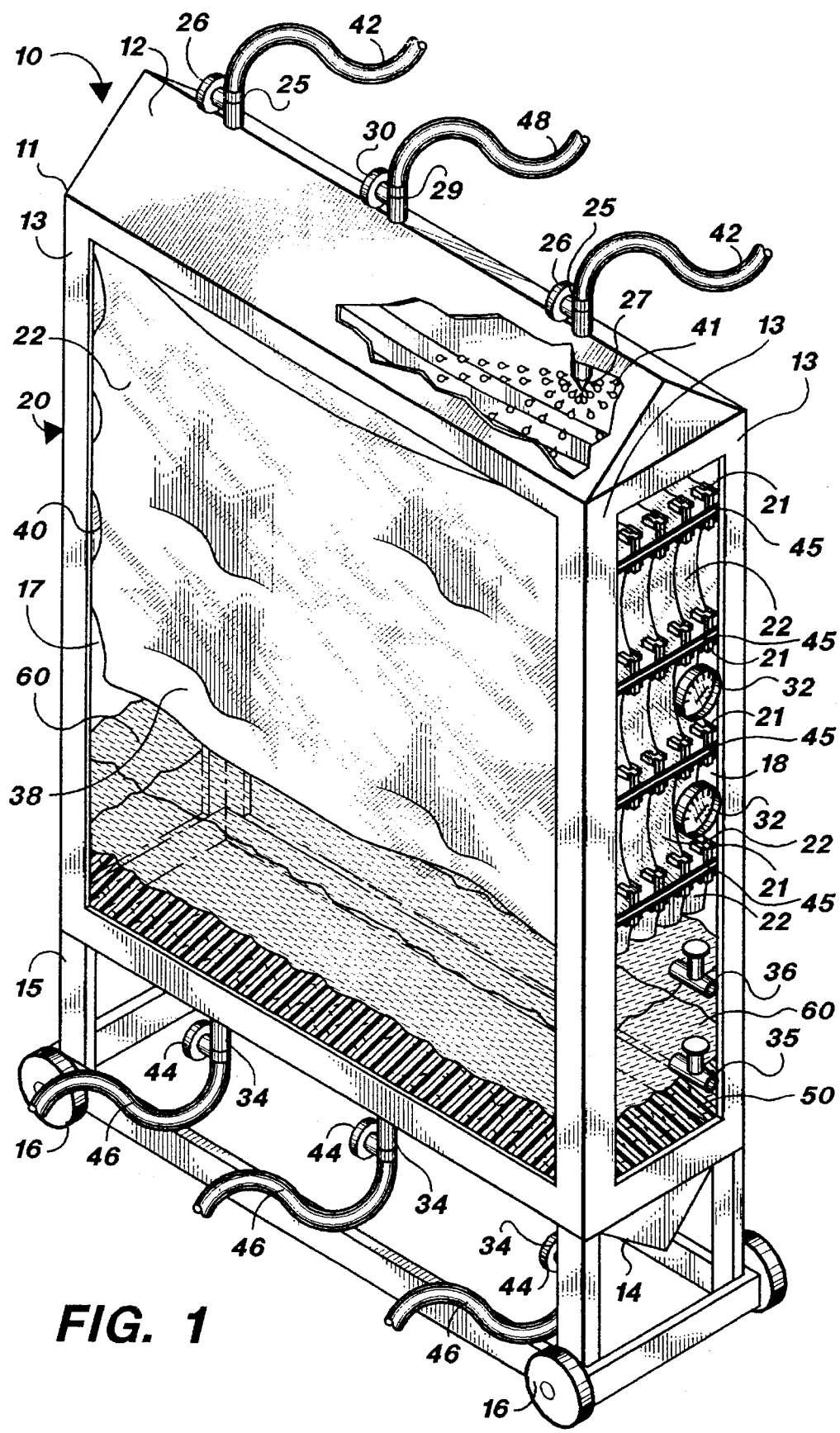
FIG. 1 is a perspective view of the bioreactor of the present invention.

In the drawings, wherein the same or similar features are designated with the same reference numerals, the bioreactor of the present invention is shown generally at 10. The primary purpose of the bioreactor 10 is to grow cells, e.g. microorganisms, bacteria, and animal, plant, fungi, and other cells, and/or cause them to produce a desired by-product, e.g. acids, enzymes, saccharides, vitamins, proteins, etc. For example, the bioreactor 10 shown in the drawings has been used to produce yeast. Similarly, the bioreactor 10 could be used to stimulate cells into producing acetic acid, citric acid, ethanol, acetone, butanol, lactic acid, and other by-products. Further, while the term "cell" is used to describe the matter grown and utilized within the bioreactor 10 (wherein "cell" is generally understood to mean a microscopic structure including at least a cell membrane and nuclear material), the bioreactor 10 is not limited to the culture of "cells" strictly following that meaning. The bioreactor 10 of the present invention may also be used to culture organisms, viruses and enzymes and/or recover products from organisms, viruses and enzymes. Nevertheless, this disclosure will adhere to the use of the term "cell", this term being understood to encompass matter which does not fit the standard definition of "cell".

The bioreactor 10 includes a frame housing 11, which includes a roof 12, corner brackets 13, and a base 14. In the preferred embodiment of the invention, these components are made of steel sheet which is bolted and welded together. Other materials and manufacturing methods for producing the frame housing 11 are possible. For example, the frame housing 11 may be a molded single-piece plastic frame housing 11, or even a wooden frame housing 11 held together by glue, nails, or screws.

The frame housing 11 may include a support cart 15, which optionally includes wheels 16 and which should have sufficient strength to support the bioreactor 10 when it is in normal operation. Thus, it is suggested that the support cart 15 be made of welded steel channel or a similarly strong metal structure.

The bioreactor 10 should be capable of being opened so that an operator may access its interior for cleaning and maintenance. In the preferred embodiment of the bioreactor 10, the roof 12 is hinged to the remainder of the frame housing 11 so that it may be lifted therefrom, and a rubber seal (not shown) is provided about the roof 12 so that it forms a water-tight (and preferably air-tight) seal with the remainder of the frame housing 11. Other access parts may be incorporated on other parts of the bioreactor 10 to facilitate operations within the bioreactor 10.

The frame housing 11 supports two opposing face walls 17 and two opposing side walls 18. In the preferred embodiment, the face walls 17 and side walls 18 are made of planar plexiglass sheet which is bolted and epoxied to the corner brackets 13 of the frame housing 11 to produce a water-tight and air-tight tank 20. The face walls 17 and side walls 18 may be made of other materials having other configurations, e.g. glass, sheet steel, or plastic. However, it is preferable that the walls 17 and 18 be made of a material which may function as a wall of the tank 20 without leakage, breakage, corrosion, or undue wear when the bioreactor is in normal operation. Planar walls 17 and 18 are recommended for the tank 20 because they are easier to clean. Additionally, transparent face walls 17 and side walls 18 have the advantage that they allow visual monitoring of the processes within the tank 20. Plexiglass is a good candidate for the material of the face walls 17 and side walls 18 of the tank 20 because of its transparency, and because it is generally more durable than glass.

Although a number of different tank 20 configurations are possible (e.g., round tanks, triangular tanks, etc.), it is preferable that the face walls 17 be planar and parallel to one another, and that the side walls 18 also be planar and parallel to one another, so that a box-like rectangular tank 20 is formed. This allows an extremely space-efficient organization of multiple bioreactors 10 when the tanks 20 are located each adjacent to one another, with at least one face wall 17 abutting (or nearly abutting) a face wall 17 of an adjacent bioreactor 10. By organizing multiple bioreactors 10 in this manner, the multiple bioreactors 10 can be placed in a row in close-packed fashion, similar to a row of books on a bookshelf. Each single bioreactor 10 may then be pulled from the row by use of the wheels 16 on the base 14 for maintenance and repair. Multiple bioreactors 10 may fit within a relatively small area, allowing the practical use of multiple bioreactors within the same room or laboratory space. Different cells may then be grown in the same room in different bioreactors 10 with different tank 20 conditions. Maintenance and cleaning of individual bioreactors 10 may be achieved with no repair down-time for the remaining bioreactors 10 by pulling the bioreactor 10 to be serviced from the row and leaving the other bioreactors 10 untouched.

The bioreactor 10 includes within its tank 20 an immobilization matrix having one or more cell support surfaces for entrapping and harboring the cells to be cultured. The cell support surfaces of the bioreactor 10 are one or more cell support sheets 22, each of which has a sheet-like configuration with two generally planar faces 38 bounded by sheet edges 40. While the invention may utilize prior art cell support surfaces, it preferably uses a cell support sheet 22 made of a common textile fabric having an interwoven organic or synthetic fibrous structure. Examples of such common textile fabrics are fabrics made of woven, knitted, felted, or meshed plant, animal, and synthetic fibers, such as terry cloth, felt, flannel, burlap, tweed, velvet, khaki, wool linen, canvas, VELCRO, etc. In the use of the bioreactor 10 of the present invention, such common textile fabrics have been found to be well suited for use as cell support sheets 22 because their fibrous structure allows for the entanglement and immobilization of cells in the interstices between fibers. In addition, such common textile fabric cell support sheets 22 have several significant advantages over prior art cell support surfaces: they can be easily washed for reuse; they can be easily sterilized; and they are available at a cost which is dramatically lower than typical prior art cell support surfaces. In addition, textile fabrics are extremely workable surfaces which may be quickly trimmed to size and sewn (or otherwise altered) if modifications to the cell support sheets 22 are desired. It has been found that a textile fabric generally functions better as a cell support sheet 22 if it is highly porous and has a coarse surface, since these characteristics provide cells with more nesting sites in surface voids and interstices between fibers. In the preferred embodiment, the cell support sheets 22 are common household terry-cloth towels or towel-like material that can be purchased from a department store.

The tank 20 includes support means for supporting the cell support sheets 22 within the tank 20 in some desired configuration, thereby creating the immobilization matrix. Such support means is generally necessary since the cell support sheets 22, generally being common textile fabrics, do not have the structural rigidity to support themselves within the tank 20. In the preferred embodiment of the bioreactor 10, the support means are provided in the form of sheet supports 45 which include clips 21. The sheet supports 45 are attached to the corner brackets 13 so that the clips 21 are arrayed in regularly spaced intervals along the length of the side walls 18. The clips 21 are spring-actuated pincers which are normally in a closed position, but which open when grasped. Such clips 21 make the cell support sheets 22 extremely easy to install within the tank 20 or remove for cleaning or replacement. Since the clips 21 hold the cell support sheets 22 at their sheet edges 40, the weight of the cell support sheets 22 maintains them in a vertical orientation. As will be discussed shortly, the vertical orientation is beneficial for a cost-efficient bioreactor 10 because it allows gravity to assist the delivery of nutrient cell culture solution to, and recovery of cell product from, the faces 38 of the cell support sheets 22. Additionally, the vertical orientation of the cell support sheets 22 and the regular spacing of the clips 21 along the sheet supports 45 produce a parallel layered immobilization matrix of cell support sheets 22 wherein the sheets 22 do not need any spacers to hold their faces 38 apart. Such spacers are undesirable since they may interfere with nutrient delivery, gas circulation, and/or cell product recovery, and they additionally occupy space on the faces 38 of the cell support sheets 22 which could otherwise be used to harbor cells. Such spacers also tend to increase the pressure within the bioreactor.

While the preferred embodiment of the bioreactor 10 utilizes support means in the form of sheet supports 45 which include regularly spaced clips 21, other forms of support means may be used. For example, the sheet supports 45 may be attached to the face walls 17, side walls 18, or other parts of the frame housing 11, such as the roof 12 or corner brackets 13. Instead of using clips 21, the sheet supports 45 may use other fixture means for affixing the cell support sheets 22 to the sheet supports 45, such as various fasteners (screws, staples, etc.), hooks, ties, or bars or rods whereupon the sheets 22 may be draped.

In addition, the support means may arrange the cell support sheets 22 into a different style of immobilization matrix. The vertical parallel layered immobilization matrix of the bioreactor 10 has many advantages, such as gravity-assisted nutrient feed and cell product recovery, tank space economy, and elimination of the need for spacers between the cell support sheets 22. However, many of the advantages of the vertical parallel layered matrix can also be had if the immobilization matrix is at an angle to the vertical. The clips 21 may be repositionable along the sheet supports 45 so that they can be moved to allow the cell support sheets 22 held within the clips 21 to rest with their faces 38 at an angle to the vertical. For instance, the cell support sheets 22 may be placed in a parallel array wherein the face 38 of each cell support sheet 22 is at a 45 degree angle to the vertical. Spacers are still unnecessary provided the clips 21 (or other fixture means) are strong enough to hold the cell support sheets 22 taut so that they do not relax and contact cell support sheets 22 below.

However, an immobilization matrix wherein the cell support sheets 22 rest at angles varying from the vertical will generally require compromises to be made in the size of the tank 20 and the cost and efficiency of the nutrient feed system and the cell product recovery system. For example, some cell product may accumulate on the top faces 38 of the cell support sheets 22, making its recovery more difficult. Also, the nutrient cell culture solution may drip from the upper faces 38 of the cell support sheets 22 before flowing to the lower portions of their faces 38, thereby lessening the amount of nutrients supplied to the cells harbored in the lower faces 38. In addition, a parallel layered immobilization matrix at an angle to the vertical will generally require a wider tank 20 with larger side walls 18 unless a lesser number of (or smaller) cell support sheets 22 are used. Such wider tanks 20 reduce the possibility (and efficiency) of using a close-packed row arrangement of bioreactors 10.

It is also possible that the bioreactor 10 may use a vertical parallel layered immobilization matrix wherein the cell support sheets 22 are not maintained in their planar form. The cell support sheets 22 may be bended from a planar configuration to a curved or coiled configuration. For example, each cell support sheet 22 within the immobilization matrix may be bent into the shape of a U, with each sheet 22 resting within the curve of an adjacent sheet 22. Another possibility is that the cell support sheets 22 may be bent into tubular forms, with a number of such sheets 22 hung vertically in a concentric array. However, these immobilization matrix configurations will also generally require a wider tank 20 than would a bioreactor 10 with a vertical parallel immobilization matrix utilizing planar cell support sheets 22.

The tank 20 preferably includes feed means for supplying nutrients to the cells harbored on the cell support sheets 22 within the tank 20. The feed means may be no more than the hingedly attached roof 12 of the tank 20, whereby an operator may open the roof 12 and sprinkle nutrient cell culture solution onto the cell support sheets 22. However, the recommended form of the feed means is a feed inlet 25 (or several feed inlets 25) at the roof 12 or on an upper portion of the tank 20. The feed inlet 25 preferably includes a feed nozzle 27 which produces a gravity-aided wide-dispersion spray or mist of nutrient cell culture solution so that nutrients are supplied to substantially the entire faces 38 of the cell support sheets 22. In FIG. 1, this mist is shown at 41. If desired, feed hoses 44 may be attached to the feed inlet 25 so that nutrient cell culture solution can be supplied from tanks (not shown).

If a very tall tank 20 is used, i.e. the cell support sheets 22 are very long, it may be difficult for the feed nozzles 27 to supply the entire faces 38 of the cell support sheets 22 with nutrient cell culture solution. This may be remedied by providing a feed inlet 25 at the roof 12 wherein the feed nozzles 27 are replaceable with feed nozzles 27 of different sizes and spray dispersion qualities. For example, in FIG. 1, a shorter feed nozzle 27 would rest higher in the tank 20 and would therefore cover more of the cell support sheets 22. A feed nozzle 27 which produces a finer mist 41 is also helpful. Alternatively, the feed nozzle 27 and feed hose 42 may constitute a unit separate from the feed inlet 25 which may be inserted within the tank 20 through the feed inlet 25. The feed nozzle 27 may then be raised or lowered by simply grasping the feed hose 42 at the outside of the tank 20 near the roof 12 and maneuvering the feed nozzle 27 to different heights within the tank 20. Finally, the dispersion of the nutrient cell culture solution may also be varied by altering the flow rate of the nutrient cell culture solution so that it will collect on the upper portions of the faces 38 of the cell support sheets 22 and then trickle down their faces 38 to supply the cells on the lower portions of the faces 38 with nutrients. A feed spigot 26 may be provided to regulate the flow of nutrient cell culture solution through the feed nozzle 27.

Despite the preceding discussion, it is rarely necessary to manipulate the feed nozzle 27 or the nutrient flow rate in order to supply the entire cell support sheet 22 with nutrients. Since the preferred embodiment of the bioreactor 10 utilizes cell support sheets 22 made of common textile fabric, some nutrient cell culture solution flows by gravity through unoccupied interstitial capillaries between the fibers of the cell support sheets 22. This nutrient flow within the cell support sheet 22 often serves to supply the lower portions of the faces 38 with sufficient nutrients.

If a feed inlet 25 is used to supply the interior of the tank 20 with nutrient cell culture solution, excess solution will generally tend to build up in a pool 60 near the base 14 of the tank 20 and gradually fill the tank 20 unless some means of draining the excess solution is provided. Thus, a fluid outlet 35 may be included on the tank 20 to allow excess nutrient cell culture solution (or waste liquid or a desired liquid cell product) to be drained from the tank 20. The fluid outlet may be provided on the base 14, the face walls 17, the side walls 18, or elsewhere on the tank 20.

Similarly, the cells on the cell support sheets 22 will produce cell products which will fall from the faces 38 of the cell support sheets 22 and collect in the base 14 of the tank 20 (as shown in the Figures by the layer of product 50). It is therefore recommended that the base 14 (or the walls 17 or 18 near the base 14) include product recovery means for recovering the cell product from the tank 20. The product recovery means may take the form of at least one cell product recovery outlet 34 through which solid or liquid cell product may be removed. These cell product recovery outlets 34 are shown in FIGS. 1–3 with spigots 44 and hoses 46 attached. Alternatively, the cell product may be scooped or vacuumed from the tank 20 (perhaps from access through the roof 12), but this method can be difficult and time-consuming. The cell product recovery outlets 34 greatly ease the removal of cell product when compared to other manual methods of removal. Where the cell product is a fluid, the fluid outlet 35 may be used to recover the cell product.

The preferred embodiment of the bioreactor 10 is a gas/liquid phase bioreactor wherein at least one of the faces 38 of the cell support sheets 22 are substantially surrounded by gas, rather than fluid (e.g. nutrient cell culture solution). If the bioreactor 10 is to be operated as a gas phase bioreactor, it is recommended that the tank 20 include at least one gas inlet 29 through which the desired gas may be input to the tank 20. In FIGS. 1–3, a single gas inlet 29 is located on the roof 12, but it may instead be located on the face walls 17, side walls 18, base 14, etc. A hose 48 for supplying gas to the gas inlet 29 is shown. The gas inlet 29 preferably includes a gas inlet spigot 30 for regulating the flow of the gas. If a gas inlet 29 is used, the tank 20 should be airtight as well as watertight so that the input gas is not wasted by leakage to the surrounding environment. If a gas inlet 29 is used, it is also recommended that at least one gas outlet 36 be located somewhere on the tank 20 so that produced, excess or waste gases may be vented. In the Figures, the gas outlet 36 is located on a side wall of the tank 20. The gas outlet 36 may include (or may be no more than) a gas overflow valve which opens when the pressure of the gas within the tank 20 exceeds some predetermined level.

Operation of the Bioreactor

To prepare the bioreactor 10 for operation, the cell support sheets 22 are hung upon the clips 21 within the tank 20 so that they are configured to form the desired immobilization matrix, e.g. a vertical parallel layered immobilization matrix. The cell support sheets 22 are wetted and then impregnated with a cell, e.g. yeast. The cell support sheets 22 may be impregnated or coated by sprinkling them with cell cultures, spraying them with a solution containing these cells, or employing similar means for introducing cells into the pores/voids within the surface of the cell support sheets 22 or onto the surfaces of the cell support sheets 22. The cell support sheets 22 are preferably sterilized before impregnation so that the sheets 22 are not additionally contaminated with unwanted types of bacteria or other cells.

The gas inlet(s) 29, if provided, can then be used to introduce a desired gas (e.g. nitrogen, $CO_2$ oxygen) into the tank 20. The gas phase can have a large effect on the cell product output. For example, if yeast are left to feed in an aerobic environment, they will produce more yeast; if they are left in an anaerobic environment, they will produce ethanol. Thus, by tailoring the gas phase to the specific needs of the cells, specific cell products and greater cell product yields may often be obtained. The gas outlet 36 may be used to vent desired, excess or waste gases from the tank 20. Gas may also be recirculated if desired.

In the liquid phase, if a feed inlet 25 (or multiple feed inlets 25) is included, a nutrient cell culture solution may then be supplied to the faces 38 of the cell support sheets 22 so that the cells may feed. The nutrient cell culture solution may be a liquid carbohydrate solution, such as liquid sugar. Alternatively, the roof 12 of the tank 20 may be opened and nutrients may be poured or sprinkled onto the cell support sheets 22. However, the feed nozzles 27 allow a much more convenient and precise means of supplying the cells with nutrients, and they also generally provide a more uniform nutrient supply over the faces 38 of the cell support sheets 22.

Product yields from the bioreactor 10 may also be increased if the environment within the tank 20 is regulated to produce optimum temperature and pressure conditions for the cells. Temperature and pressure within the tank 20 may be measured at gauges 32. The temperature within the tank 20 may be left at ambient or it may be altered by the temperature of the inlet gas or inlet nutrient cell culture solution, or by use of heating elements. For example, one simple and economical means of providing desired heating to the tank 20 is to wrap commonly available pipe heating/cooling coils about the tank. Alternatively, heating/cooling apparatus may be installed within the tank 20 near the roof 12 or elsewhere. The appropriate gas may be supplied at the appropriate pressure by use of the gas inlet spigot 30. Thus, the bioreactor 10 allows the environment and the diet of the cells to be modified for optimum cell product yield.

As the cells release the desired cell products, the cell products fall from the cell support sheets 22 and tumble down the faces 38 of the sheets 22 due to the action of gravity. The action of excess nutrient solution washing down the faces 38 of the cell support sheets 22, or flowing from intra-fibral capillaries within the cell support sheets 22 to the sheet faces 38, can also assist in the removal of cell product from the sheets 22. Gas flow may also assist in removing cell product from the sheets. The cell product then falls into the pool 60 at the base 14 of the tank 20, which contains excess nutrient solution, cell product, dead cells, and so forth. FIG. 1 illustrates the appearance of the bioreactor 10 when yeast is stimulated into producing more yeast, the cell product to be harvested. The product yeast collects and settles in the base 14 of the tank 20, as illustrated by the layer of cell product 50. The cell product recovery outlet(s) 34 can be used to remove solid or liquid cell product from the base 14, or if no cell product recovery outlet 34 is provided, the cell product may be scooped or vacuumed from within the tank 20. A desired liquid cell product can also be removed by means of the fluid outlet 35, which is otherwise intended to remove excess or waste fluid. This liquid from the fluid outlet 35 can be recycled through the feed inlet 25 if it is sufficiently rich in nutrient content; alternatively, the liquid from the fluid outlet 35 can be partially or wholly replenished with carbohydrates or similar nutrient ingredients, and then recycled through the feed inlet 25. In typical usage, the feed inlet 25 is continuously supplied with nutrient solution, the gas inlet 29 is continuously supplied with gas, and the cell product recovery outlet 34, fluid outlet 35 and gas outlet 36 are continuously drained. Thus, the cell product and fluid within the tank 20 are kept at a steady level.

It is understood that the invention is not confined to the particular construction and arrangement of parts herein illustrated and described, but embraces such modified forms thereof as come within the scope of the following claims.

What is claimed is:

1. An immobilized cell bioreactor apparatus for culturing immobilized cells which produce cell product or by-product upon or within at least one cell support sheet including two faces bounded by a sheet edge, the apparatus comprising:

a. a tank including a base, a roof, two opposing face walls, and two opposing side walls, the tank further including support means for supporting at least one cell support sheet within the tank from the sheet edge so that the faces are maintained in a substantially vertical orientation;

b. a generally planar cell support sheet wherein cells may be immobilized, the cell support sheet having two faces bounded by a sheet edge, with a gas phase bounding at least substantially one entire face of the cell support sheet;

c. feed means for dispensing nutrient feed stock into the tank; and d. product recovery means for recovering a product produced by the cultured cells.

2. The immobilized cell bioreactor apparatus of claim 1 comprising a plurality of cell support sheets arranged in parallel fashion.

3. The immobilized cell bioreactor apparatus of claim 1 wherein the cell support sheet is comprised of a common textile fabric material chosen from terry cloth, felt, flannel, burlap, tweed, velvet, khaki, wool, polyester, linen, and VELCRO.

4. The immobilized cell bioreactor apparatus of claim 1 wherein the cell support sheet is comprised of terry-cloth.

5. The immobilized cell bioreactor apparatus of claim 1 wherein the feed means comprise a feed nozzle through which nutrient feed stock may be dispensed, the feed nozzle being located on the tank generally above the cell support sheet.

6. The immobilized cell bioreactor apparatus of claim 1 wherein the feed means comprise a feed spigot for regulating the flow of nutrient feed stock.

7. The immobilized cell bioreactor apparatus of claim 1 wherein the product recovery means comprise a product recovery outlet located on the tank generally below the cell support sheet.

8. The immobilized cell bioreactor apparatus of claim 1 further comprising a gas inlet located on the tank and additionally a gas outlet located on the tank.

9. The immobilized cell bioreactor apparatus of claim 8 wherein the gas outlet is a gas overflow valve for venting gas from the tank when its pressure exceeds a preset limit.

10. The immobilized cell bioreactor apparatus of claim 1 further comprising a fluid outlet located on the tank.

11. The immobilized cell bioreactor apparatus of claim 1 wherein the face walls and side walls are transparent.

12. The immobilized cell bioreactor apparatus of claim 1 wherein the face walls are generally parallel to each other and the side walls are generally parallel to each other.

13. The immobilized cell bioreactor apparatus of claim 1 further comprising a support cart for supporting the tank.

14. The immobilized cell bioreactor apparatus of claim 13 wherein the support cart includes wheels.

15. A method for culturing immobilized cells which produce cell product or by-product, the mobilized cells being harbored within or upon at least one cell support sheet having two faces bounded by a sheet edge, in an immobilized cell bioreactor which includes a tank having a base, a roof, two opposing face walls, and two opposing side walls, the bioreactor further including the cell support sheet and support means for supporting the cell support sheet within the tank from the sheet edge so that the faces are maintained in a substantially vertical orientation, the method comprising the steps of:

a. introducing the cells onto the cell support sheet;
 b. introducing nutrient feed stock into the tank at a location generally above the cell support sheet;
 c. forming a spray of droplets from the nutrient feed stock at a location above the cell support sheets so that a substantial portion of the spray falls onto the faces of the cell support sheets; and
 d. recovering cell product or by-product produced by the cells.

16. The method for culturing immobilized cells of claim 15 including a step preceding step (a) comprising sterilizing the cell support sheets.

17. The method for culturing immobilized cells of claim 15 including a step preceding step (b) comprising regulating the temperature within the tank to correspond to the temperature at which the cells yield the greatest amount of product.

18. The method for culturing immobilized cells of claim 15 including a step preceding step (b) comprising regulating the pressure within the tank to correspond to the pressure at which the cells yield the greatest amount of product.

19. The method for culturing immobilized cells of claim 15 when the step of supplying the nutrient feed stock to at least a portion of the faces of the cell support sheets comprises supplying nutrient feed stock to an uppermost portion of the sheet edge so that the nutrient feed stock flows downward within the cell support sheets.

20. An immobilized cell bioreactor apparatus comprising:

a. a tank;
 b. a generally planar cell support sheet wherein cells may be immobilized, the cell support sheet having two faces bounded by a sheet edge, the cell support sheet being located within the tank with a gas phase bounding at least substantially one entire face of the cell support sheet;
 c. feed means for dispensing nutrient feed stock onto the cell support sheet; and
 d. product recovery means for recovering a product produced by the cultured cells.

* * * * *